Figure 1:
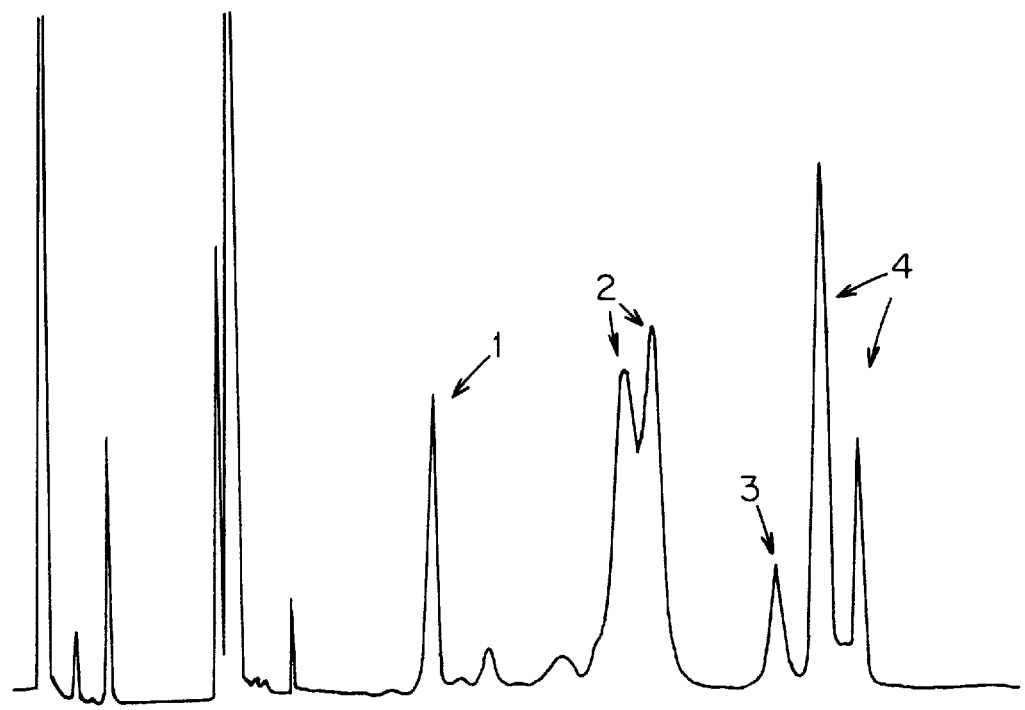

United States Patent [19]

Erlansson et al.

[11] Patent Number: 5,872,227
[45] Date of Patent: Feb. 16, 1999

[54] PROCESS FOR SEPARATION OF COMPONENTS FROM RED BLOOD CELLS

[75] Inventors: Karin Erlansson, Lund; Hans Jungvid, Veddige; Bo Mattiasson; Göran Nilsson, both of Lund; Thomas Olin, Täby; Torbjörn Sund, Lund, all of Sweden

[73] Assignee: Gramineer AB, Veddige, Sweden

[21] Appl. No.: 530,362

[22] PCT Filed: Apr. 8, 1994

[86] PCT No.: PCT/SE94/00314

§ 371 Date: Oct. 6, 1995

§ 102(e) Date: Oct. 6, 1995

[87] PCT Pub. No.: WO94/23729

PCT Pub. Date: Oct. 27, 1994

[30] Foreign Application Priority Data

Apr. 8, 1993 [SE] Sweden ................................... 9301188

[51] Int. Cl.⁶ .............................. G01N 33/49; A23J 1/06; A23J 3/12; A61K 35/14
[52] U.S. Cl. .......................... 530/412; 530/385; 530/829; 435/183; 435/317.1; 424/647; 424/529; 426/647
[58] Field of Search ..................... 424/529, 647; 426/647; 435/183, 317.1; 530/829, 385, 412

[56] References Cited

U.S. PATENT DOCUMENTS 4,376,727  3/1983  Sato .
4,610,814  9/1986  Dede .

FOREIGN PATENT DOCUMENTS

A-026417   4/1981   European Pat. Off. .
0217849    3/1990   European Pat. Off. .
A-438192   7/1991   European Pat. Off. .
A-520185   12/1992  European Pat. Off. .
940-066    12/1979  U.S.S.R. .
1 205 910  1/1986   U.S.S.R. .
A-1 430 217 10/1973 United Kingdom .

OTHER PUBLICATIONS

Senstad, C. and Mattiasson, B.; Biotechnology and Bioengineering 34, pp. 387–393, 1989; Purification of Wheat Germ Agglutinin Using Affinity Flocculation with Chitosan and a Subsequent Centrifugation or Flotation Step.

Dialog Information Services, File 73, Embase, Dialog accession No. 1464221, Embase accession No. 79234798; Chuillon, J. et al.; J. Fr. Biophys. Med. Nucl. (France), 1979, 3/3 (121–126).

Patent Abstracts of Japan, "Hepatitis–Free Haemoglobin Solutions", vol. 85, No. 25, abstract of JP, A, 85–25411, 1985.

Sigma catalog 1992 pp. 511–513 and 792–799.

*Primary Examiner*—Toni R. Scheiner
*Assistant Examiner*—Nancy A. Johnson
*Attorney, Agent, or Firm*—McDermott, Will & Emery

[57] ABSTRACT

Disclosed is a process which achieves effective separation of components from red blood cells by aggregating cell membranes with an addition of a pH lowering agent, whereupon the solution is made subject to a separation step where a water soluble fraction is separated from cell membranes, and whereupon the cell membranes are extracted, and where lipids may be selectively separated and recovered by lowering the temperature of the extract.

15 Claims, 1 Drawing Sheet

PROCESS FOR SEPARATION OF COMPONENTS FROM RED BLOOD CELLS

This application is a 371 of PCT/SE94/00314 filed Apr. 8, 1994.

DESCRIPTION

1. Technical Field

The present invention is related to a process for separation of components from red blood cells.

The object of the invention is to facilitate separation of cell membranes from a water soluble fraction. The invention thereby enables effective manufacture of raw material for preparation of membrane-bound lipids from red blood cells. A further object of the invention is to facilitate purification of components from a water soluble fraction of red blood cells, by reducing the lipid content of such water-soluble preparation. A further object is to facilitate preparation of glycolipids or phospholipids in a lipid extract of said membranes.

2. Background of the Invention

In separation of cell membranes and a water soluble fraction from red blood cells for analytical and preparative purposes, usually a centrifuge method is employed. An effective separation of native cell membranes from a water soluble fraction requires a great gravitational force. High gravitational forces and an acceptable product flow could not be combined on processing of red blood cells on an industrial scale. This has lead to low yields of cell membranes.

With the purpose of increasing the yield of blood fractions on centrifugal preparation, supplementary techniques have been developed, for example a system of blood bags in combination with pressure cushions (EP-A-026417) and synthetic gels which separate cells from a water soluble fraction (EP-A1-520185). These techniques are effective on processing of small volumes of blood, but they are not suitable for industrial production.

Further, a filtration technique is employed for enrichment of whole red blood cells or specific fractions (Japanese Patent Application No. 61,181,963, U.S. Pat. No. 4,946,603). Cell membranes, however, disturb the filter, thus that the flow is limited, and thereby the capacity of the process is reduced.

It is previously known that aggregation or agglutination of blood cells can be achieved by cross-linking the negative surface charges of the blood cell with amine polymers such as polylysine (EP-A-438192) and chitosan (Senstad C. and Mattiasson B. Biotechnology and Bioengineering 34(3), 387–393, 1989). This type of aggregation can facilitate separation of blood cells from a water soluble fraction. Production of polylysine is resource-demanding, which limits the utility as means for aggregation of cell membranes on an industrial scale. Chitosan aggregates cell membranes, but simultaneously increases the viscosity of the solution. The increased viscosity counteracts the sedimentation of cell membranes induced by the aggregation. The cross linking amine polymers adhere to components of the surface of the cell membrane, e.g. sialic acid on glycolipids and glycoproteins. On preparation of native forms of e.g. biologically active glycolipids, an extra separation step may be required, which removes bound amine polymer.

GB-A-1430 217 describes a process for the preparation of an infusible storage-stable haemoglobin solution by haemolysing an erythrocyte-containing starting material with β-propiolactone, washing out the β-propiolactone, and separating the stroma from the hemoglobin solution by binding the stroma to a cation exchange material at pH 5.0 to 5.5.

SU Inventor's Certificate 940 066 describes a process for production of haemoglobin and stroma for medical use. Erythrocytes in buffer solution are haemolysed in a buffer solution, in particular a sodium phosphate buffer of pH 6.1–6.5, followed by separation of the free haemoglobin from cell stroma by binding of hemoglobin to a cation exchange material while the stroma remains in the surrounding medium.

DESCRIPTION OF THE INVENTION

The present invention provides a process for recovering one or more components from red blood cells, whereby a composition comprising red blood cells is made subject to a separation step where lipid-containing cell membranes and water soluble components are separated, and whereby the lipid containing cell membranes are made subject to lysis. The process is characterized in, that a water soluble pH lowering agent is added to the composition comprising red blood cells, to the aggregation of the cell membranes, for facilitating the subsequent physical separation step wherein the composition is divided into a hemoglobin-enriched, water soluble fraction substantially free from lipid containing cell membranes, and a fraction enriched in lipid containing cell membranes, whereupon one or more components are recovered from the fraction enriched in lipid containing cell membranes and/or from the hemoglobin enriched water soluble fraction.

Preferred embodiments of the invention will be evident from the following description and claims.

Two particularly preferred methods of the invention are as follows:

1. Red blood cells are lysed by an addition of 2 volumes of water. Citric acid is added to the solution with further 1 volume of water to pH 5. Interaggregated cell membranes are separated from a water soluble fraction with a centrifugal separator or corresponding physical separation technique, such as filtration, in particular membrane filtration, flotation, sedimentation or decantation or other techniques wherein a difference in density or viscosity is employed. Cell membranes are extracted with ethanol, the extract is incubated at 4° C. The glycolipid-enriched precipitate is separated. The water soluble fraction is further purified with a chromatographic technique.

2. Red blood cells are lysed by an addition of 2 volumes of water. Hydrochloric acid is added to the solution to pH 5.5. Aggregated cell membranes are separated from a water soluble fraction with a centrifugal separator or corresponding technique. The water soluble fraction is further purified with a chromatographic technique. Cell membranes are extracted with ethanol, the extract is incubated at −20° C. The glycolipid-enriched precipitate is separated.

The present invention enables effective separation of components from red blood cells by aggregating cell membranes with an addition of a pH lowering water soluble agent, whereupon the solution is made subject to a separation step where a water soluble fraction is separated from cell membranes, whereupon the cell membranes are extracted, and where lipids are selectively separated and recovered by lowering the temperature of the extract.

Phospholipids and glycolipids are the major classes of cell membrane lipids. Pathogenic bacteria often bind to glycolipids on a tissue surface. The attachment of bacteria is the initial event in many infectious processes. An extensively characterized example is the binding of uropathogenic E. coli to the globo series of glycolipid receptors. Free glycolipids administered are able to inhibit the binding and persistence of such bacteria on a tissue surface. This type of receptor activity is fundamental for the development of new therapeutic and diagnostic products.

Phospholipids may be used as carriers to provide nutritionally essential fatty acids. Further, phospholipids are used in various products, for example as an emulsifying agents in food and cosmetics and as part of liposomes in drug delivery systems.

The lipids may be used either as an additive to nutritional products or prepared as a pharmaceutical composition. As examples of pharmaceutical compositions may be mentioned tablets, drops, suppositories, preparations for topical applications such as ointments, jellies, creams, powders, drops and suspensions. Usually, the active substance will constitute 0.01% to 99% by weight of the composition, or for example from 0.05% to 50% for preparations intended for oral administration, and from 0.05% to 80% for preparations intended for topical application.

Further, the lipids may be used as a specific ligand for a pathogen or a toxin for diagnostic purposes.

The invention relates particularly to a process for facilitating enrichment of glycolipids, phospholipids, cholesterol or membrane proteins from cell membranes, and hemoglobin, glucose-6P-dehydrogenase, 2,3-diphosphoglycerate and ATP from the water soluble fraction of red blood cells.

Aggregation of cell membranes is carried out with an addition of a pH lowering agent causing a change of the forces otherwise holding the cells apart. The exploited mechanism of the aggregation of cell membranes is, contrary to that of amine polymers, not of a cross linking nature, since also monovalent acids are functional. Aggregation of cell membranes with a pH lowing agent does not modify surface structures and is thereby suitable for preparation of e.g. biologically active glycolipids.

Aggregated cell membranes have a higher coefficient of sedimentation than have untreated cell membranes, which causes them to be separated from a water soluble fraction at a lower gravitational force than is otherwise possible. A combination of a technique for aggregation of cell membranes with a pH lowering agent and conventional centrifugal preparation provides an unexpectedly effective separation of cell membranes from a water soluble fraction, both for analytical purposes and for production on an industrial scale. Similar advantages are provided by the invention in combination with e.g. decantation and flotation or other techniques where a difference in density or viscosity is employed.

A further advantage is provided by the invention on separation of cell membranes from a water soluble fraction with a filtration technique. Cell membranes, which have been treated according to the present invention form large aggregates, something that reduces the risk of blocking pores in a filter. Aggregated cell membranes can also be effectively separated from a water soluble fraction out of the red blood cells with filters of a larger pore size than those filters which are required for untreated cell membranes. An increase of the pore size of the filter increases the capacity of the filtration plant.

The water soluble fraction from red blood cells prepared according to the invention is substantially free from cell membranes, thus facilitating further purification of single substances, since cell membranes interfere on micro- and ultra-filtration and separation of compounds with the aid of gel material.

The water soluble fraction from lysed red blood cells consists in its major part of hemoglobin. A hemoglobin powder prepared from a water soluble fraction, substantially free from membranes, has a low bacterial content under an extended time of storage and can more easily be compressed into tablets than a hemoglobin powder with a higher content of lipids.

From cell membranes, lipids may be extracted with organic solvents. On an extraction with certain organic solvents, such as ethanol, also compounds of contaminating nature are dissolved. These contaminating compounds are separated from lipids with a conventional chromatographic technique. This step of purification is often a limiting factor for the capacity of the process. According to the present invention proteins are separated from lipids by lowering the temperature in the extract. This temperature based technique enables a greater capacity in the process, as compared with a conventional chromatographic technique.

It is known that glycolipids can be precipitated from an organic solution by decreasing the temperature to −10° C. (Koscielak J et al., Eur J Biochem vol 37, p.214–225, 1973). A known disadvantage with this method is that large amounts of contaminating compounds are coprecipitated resulting in a low concentration of the glycolipids in the solid phase. The present invention provides a method for precipitation of glycolipids with an increased purity. The precipitation process is regulated both by temperature and polarity of the lipid solution. Further this method describes the means for separating certain phospholipids from glycolipids.

The extracted lipids can also be enriched by addition of a compound which absorbs lipids, whereupon the complex is separated from the surrounding solution. The adsorbing compound is either particulate, forms a particulate complex with the lipids, gives phase separation from the extract or binds selectively to the solid phase, and may thereby be separated from contaminants as a complex of lipids.

In preparation of food, food additives and pharmaceutical compositions it is an advantage if nontoxic process aids can be employed, since greater residual amounts of the such process aids can then be tolerated. This means in turn, lower requirements on the purification step of the manufacturing process. Nontoxic process aids also facilitate the handling of waste and is advantageous for the working environment.

The present invention encompasses use of pH lowering agents which are approved as food additives, e.g. citric acid and hydrochloric acid. Phase separation of glycolipids according to the invention replaces a chromatographic technique, which in many cases may cause contamination of the product with toxic process aids.

The invention is further illustrated with reference to examples, which are not to be considered as limiting for the invention.

DRAWINGS

Figure 2:
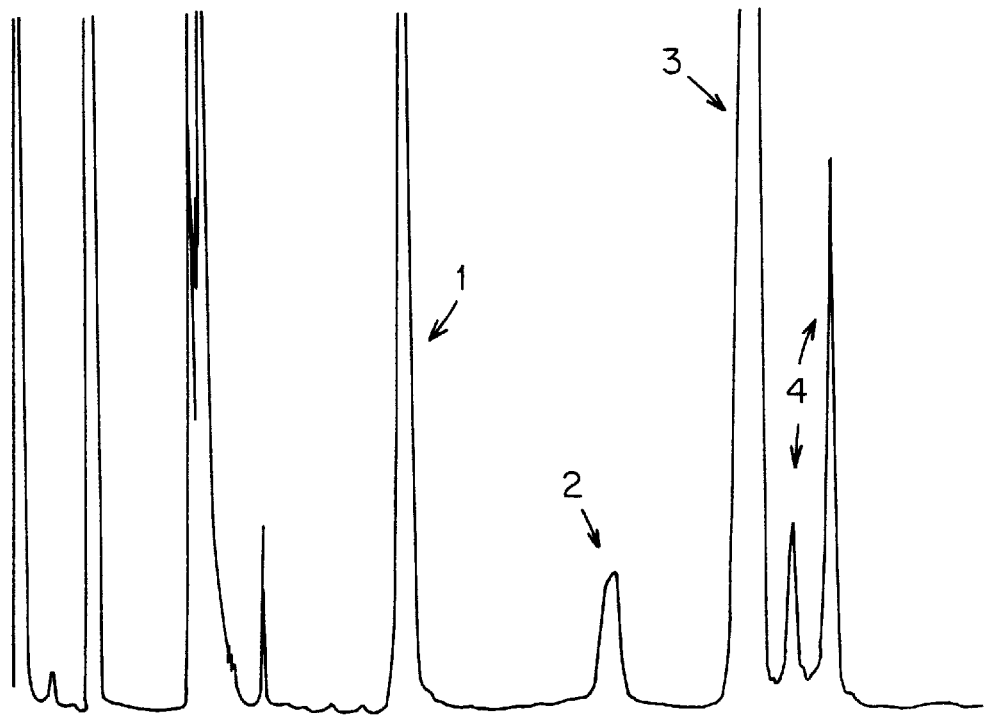

FIG. 1 is a diagram showing the distribution of lipids in a precipitate sample of Example 6 and FIG. 2 is a diagram showing the distribution of lipids in a supernatant sample of Example 6.

In the drawings, the numbers represent one or more peaks of 1: phosphatidyldiethanolamine, 2: globoside, 3: phosphatidylcholine and 4: sphingomyelin.

EXAMPLE 1

Red blood cells were made subject to lysis by an addition of two volumes of tap water. The degree of lysis was over 90%. The lysed red blood cells were divided in three equal parts which were treated as follows.

| | |
|---|---|
| Sample 1 | The sample was diluted with tap water to a final concentration of 25% red blood cells. Double samples were taken for determining the content of cell membranes. |
| Sample 2 | The sample was diluted with tap water to a final concentration of 25% red blood cells and was spun in a centrifuge (2000 g) for 10 minutes at 10° C. Double samples were taken from pellet and supernatant for determination of the amount of cell membranes. |
| Sample 3 | The sample was diluted according to the present invention with a solution of citric acid to a final concentration of 25% red blood cells and 0.5% citric acid. The sample was spun in a centrifuge (2000 g) for 10 minutes at 10° C. Double samples were taken from pellet and supernatant for determination of the amount of cell membranes |

On addition of citric acid according to sample 3 an aggregation of cell membranes was initiated. The aggregation could be monitored visually by taking out a sample and diluting with 10 volumes of water. In the sample thus diluted, filiform aggregates can be seen, which grow and separate from the hemoglobin solution.

TABLE 1

Yield of untreated and aggregated cell membranes on spinning at 2000 g, 10 min.

| | Distribution of cell membranes[1] | |
|---|---|---|
| | Pellet (product) | Supernatant (loss) |
| Sample 2 | | |
| Red blood cells + water | <10% | >90% |
| Sample 3 | | |
| Red blood cells + citric acid solution | >95% | <5% |

[1]The amount of cell membranes in pellets and supernatant, respectively, is stated in percent of the total amount of membrane specific glycolipids in the unseparated sample no 1 (see above).

Chemical analysis data showed that an effective sedimentation of cell membranes correlates well with a visually clear supernatant.

EXAMPLE 2

400 l of red blood cells (RBC) of porcine origin were lysed by addition of 400 l of tap water and incubated at 8° C. for 12 hours. The degree of lysis was over 90 percent. With the purpose of determining the efficiency with which cell membranes are separated from a water soluble fraction, the membrane-specific glycolipid globoside was quantitated. Double samples were taken from the lysed blood cells and the concentration of globoside was determined to 400 mg per liter of RBC concentrate. Lysed RBC:s were divided between four batches of 200 l and treated as follows.

| | |
|---|---|
| Sample 1 | 200 l of lysed RBC were diluted with further 100 l of tap water (total dilution 1 + 2). |
| Sample 2 | 200 l of lysed RBC were diluted with further 200 l of tap water (total dilution 1 + 3). |
| Sample 3 | 200 l of lysed RBC were diluted with further 100 l of tap water and 2, 4 kg citric acid. Aggregation of cell membranes was observed (total dilution 1 + 2). |
| Sample 4 | 200 l of lysed RBC were diluted with further 200 l of tap water and 2, 4 kg citric acid. Aggregation of cell membranes was observed (total dilution 1 + 3). |

Samples 1 to 4 were pumped separately at a rate of 50 l per hour through a centrifugal separator of the type Westfalia CSAS-06-476. Clear phase and sediment were collected separately. The content of globoside was determined in each fraction.

The yield of globoside in the sediment was markedly increased with the aggregation of cell membranes which was induced by addition of citric acid (Sample 3, Table 2). The yield of aggregated cell membranes could be increased further by an extra addition of water (Sample 4, Table 1).

TABLE 2

The effect of citric acid and dilution on the amount of globoside in pellets and clear phase on centrifugation of 100 l of RBC which was treated according to the respective sample preparation.

| | | Amount of globoside in | | |
|---|---|---|---|---|
| | Dilution | Citric acid | Sediment (product) | Clear phase (loss) |
| Sample 1 | 1 + 2 | − | 500 mg | 39500 mg |
| Sample 2 | 1 + 3 | − | 950 mg | 39050 mg |
| Sample 3 | 1 + 2 | + | 33050 mg | 6950 mg |
| Sample 4 | 1 + 3 | + | 38000 mg | 2000 mg |

The content was quantitated in the pellet and the loss calculated by subtracting the amount recovered from the total content in each batch.

EXAMPLE 3

50ml red blood cells from man (Table 3), sheep (Table 4), ox (Table 5) and pig (Table 6) were lysed each separately by an addition of 100 ml tap water. After 6 hours, the degree of lysis was over 90 percent. The lysed red blood cells from man and each animal species was divided between 11 tubes. The ability of acids to aggregate cell membranes was studied by an addition of each acid to pH 5.0. The samples were incubated at room temperature for 5 minutes. Aggregation was monitored by visual observation of a 1 ml sample which was diluted to 10 ml with water. The sample was centrifuged at 2000 g for 10 minutes. The efficiency with which cell membranes were aggregated was evaluated as turbidity (±). An effective separation of cell membranes from surrounding solution was established when the supernatant was visually clear and was rated with ±.

TABLE 3

Aggregation of lysed red blood cells from man

| Additive | Aggregation | Supernatant (visual clearness) |
|---|---|---|
| Formic acid | + | + |
| Acetic acid | + | + |
| Propionic acid | + | + |

TABLE 3-continued

Aggregation of lysed red blood cells from man

| Additive | Aggregation | Supernatant (visual clearness) |
|---|---|---|
| Butyric acid | + | + |
| Oxalic acid | + | + |
| Lactic acid | + | + |
| Citric acid | + | + |
| α-ketoglutaric acid | + | + |
| Phosphoric acid | + | + |
| Hydrochloric acid | + | + |
| Sulphuric acid | + | + |

TABLE 4

Aggregation of lysed red blood cells from sheep

| Additive | Aggregation | Supernatant (visual clearness) |
|---|---|---|
| Formic acid | + | + |
| Acetic acid | + | + |
| Propionic acid | + | + |
| Butyric acid | + | + |
| Oxalic acid | + | + |
| Lactic acid | + | + |
| Citric acid | + | + |
| α-ketoglutaric acid | + | + |
| phosphoric acid | + | + |
| Hydrochloric acid | + | + |
| Sulphuric acid | + | + |

TABLE 5

Aggregation of lysed red blood cells from ox

| Additive | Aggregation | Supernatant (visual clearness) |
|---|---|---|
| Formic acid | + | + |
| Acetic acid | + | + |
| Propionic acid | + | + |
| Butyric acid | + | + |
| Oxalic acid | + | + |
| Lactic acid | + | + |
| Citric acid | + | + |
| α-ketoglutaric acid | + | + |
| Phosphoric acid | + | + |
| Hydrochloric acid | + | + |
| Sulphuric acid | + | + |

TABLE 6

Aggregation of lysed red blood cells from pig

| Additive | Aggregation | Supernatant (visual clearness) |
|---|---|---|
| Formic acid | + | + |
| Acetic acid | + | + |
| Propionic acid | + | + |
| Butyric acid | + | + |
| Oxalic acid | + | + |
| Lactic acid | + | + |
| Citric acid | + | + |
| α-ketoglutaric acid | + | + |
| Phosphoric acid | + | + |

TABLE 6-continued

Aggregation of lysed red blood cells from pig

| Additive | Aggregation | Supernatant (visual clearness) |
|---|---|---|
| Hydrochloric acid | + | + |
| Sulphuric acid | + | + |

The results show that all acids effectively aggregate cell membranes and that the technique is useful on red blood cells from man and several animal species. The aggregation of cell membranes can also be achieved by adding a pH lowering agent without preceding lysis.

EXAMPLE 4

50ml porcine red blood cells were lysed by an addition of 100 ml tap water. After 6 hours the degree of lysis was over 90 percent. The lysed red blood cells were distributed between 16 tubes. The ability of the acids to aggregate cell membranes at varying pH was studied. The sample was titrated with the acid to a desired pH, incubated at room temperature for 5 minutes. Aggregation was established by visual observation of 1 ml sample which was diluted to 10 ml with water adjusted to the current pH. The sample was centrifuged at 2000 g for 10 minutes. The efficiency with which cell membranes were aggregated was judged as turbidity (±). An effective separation of cell membranes from the surrounding solution was established when the supernatant was visually clear. (See comment, Table 7).

TABLE 7

Aggregation of lysed porcine red blood cells

| Additive | pH | Aggregation | Comments |
|---|---|---|---|
| Citric acid | 7.0 | — | — |
|  | 6.8 | + | residue of cell membranes in supernatant |
|  | 6.0 | ++ | clear supernatant |
|  | 5.5 | +++ | clear supernatant |
|  | 4.5 | +++ | clear supernatant |
|  | 3.7 | +++ | dark-coloured aggregation, clear supernatant |
|  | 3.0 | ++ | black fine-divided precipitate |
|  | 1.0 | + | black fine-divided precipitate |
| Hydrochloric acid | 7.0 | — | — |
|  | 6.8 | + | residue of cell membranes in supernatant |
|  | 6.0 | ++ | clear supernatant |
|  | 5.5 | +++ | clear supernatant |
|  | 4.5 | +++ | clear supernatant |
|  | 3.7 | +++ | dark-coloured aggregation, clear supernatant |
|  | 3.0 | ++ | black fine-divided precipitate |
|  | 1.0 | + | black fine-divided precipitate |

EXAMPLE 5

2000l of red blood cells (RBC) were lysed by addition of 2000 l of tap water and incubated at 8° C. for 12 hours. The degree of lysis was over 90 percent. Lysed RBC:s were divided between two batches of 2000 l of and treated as follows.

| | |
|---|---|
| Sample 1 | 2000 1 of lysed RBC were diluted with further 2000 1 of tap water (total dilution 1 + 3). |
| Sample 2 | 2000 1 of lysed RBC were diluted with further 2000 1 of tap water and 2.4 kg citric acid. Aggregation of cell membranes was established (total dilution 1 + 3) |

Cell membranes from samples 1 and 2 were separated from the clear phase containing hemoglobin solution, with a centrifugal separator. Cell membranes were concentrated in a sediment. The content of the membrane specific glycolipid globoside was 0.22% in the sediment from sample 1 and 0.29% in the sediment from sample 2. Equal weights of samples 1 and 2, respectively, were extracted separately during stirring with 50 l of 80% ethanol at 80° C. The yield of globoside from aggregated cell membranes (sample 2) was 40% higher than the yield from those cell membranes which were not aggregated (sample 1). Aggregated cell membranes are easy to suspend on stirring, which gives a more efficient extraction.

EXAMPLE 6

Cell membranes were prepared from porcine red blood cells. Lipids were extracted from the membranes by 20 volumes of 80% ethanol at 80° C. for 60 minutes. The extract contained phospholipids, glycolipids and cholesterol. The solution of lipids was divided to five beakers and incubated at +20° C., +5° C., −5° C., −10° C. or −20° C. respectively. In all incubates the lipids were separated in a precipitate and a liquid phase.

Glycolipids

The precipitates formed, at all temperatures tested, were enriched with glycolipids (FIG. 1 and 2). The concentration of glycolipids increased with temperature. The concentration of the globo series of glycolipids was 3% in the extract and increased to around 20% in the precipitate formed at +5° C. to −5° C. and 30% at 20° C. (Table 8). A further increase of glycolipids in the precipitate could be achieved by a repetitive redissolving and precipitation by means described above. The time needed for precipitation of the glycolipids could be decreased by increasing the polarity of the organic solvent used.

TABLE 8

Concentration of the globo series of glycolipids in the precipitate from a lipid extract of red blood cell membranes. The precipitate was collected after incubation of the extract at −20 to 20° C.

| Incubation temperature (°C.) | Concentration of glycolipids (percent of dry matter) |
|---|---|
| −20 | 10 |
| −10 | 12 |
| −5 | 18 |
| 5 | 20 |
| 20 | 34 |

Phospholipids

There was a quality-dependent distribution of Sphingomyelin in the precipitate and the liquid phase after incubation at the temperatures described. The variable solubility of this phospholipid was correlated to its content of long chain fatty acids and the degree of saturation (FIG. 1 and 2). Phosphatidylcholine and phosphatidylethanolamine were concentrated in the liquid phase after precipitation of the glycolipids (FIG. 1 and 2).

EXAMPLE 7

Porcine red blood cells were lysed and citric acid was added to the solution to a final concentration of 0.5%, causing aggregation of cell membranes. Cell membranes were separated and extracted with ethanol, whereupon glycolipids were precipitated at 5° C. The single glycolipids were separated with TLC and incubated with radioactive labelled P-fimbriate *E. coli* (Karlsson KA and Strömberg N, Meth Enzymol 138, 220–232, 1988).

The glycolipids prepared according to the present invention bind bacteria with a high affinity, which shows that the biological activity of glycolipids is retained during the purification process according to the present invention.

Word Explanations

Aggregation: Two or more units attached to each other.

Globoside: Globotetraocylceramide, a glycolipid belonging to the globo series.

Monovalent: One-valenced, for example an acid with one proton.

Sedimentation coefficient: The rate by which a particle travels in a gravitational field. The coefficient is affected by the weight and shape of the particle. The unit is Svedberg ($10^{-13}$ s)

We claim:

1. A process for recovering at least one component from red blood cells, comprising the steps of:
   providing a composition comprising red blood cells;
   lysing the red blood cells;
   adding a water soluble pH lowering agent to aggregate cell membranes;
   physically separating the composition obtained in step 3) into a water-soluble fraction and an enriched lipid fraction; and
   recovering the at least one component from a fraction.

2. A process according to claim 1, wherein the red blood cells are lysed before the water soluble pH lowering agent is added.

3. A process according to claim 2, wherein the addition of the pH lowering agent results in a composition with a pH between about 1 to about 6.8.

4. A process according to claim 3, wherein the addition of the pH lowering agent results in a composition with a pH between about 4.5 to about 5.5.

5. A process according to claim 1, wherein the water soluble pH lowering agent is added to a final concentration between about 0.01% and about 1.5% before the red blood cells are lysed.

6. A process according to claim 5, wherein the water soluble pH lowering agent is added to a final concentration between about 0.03% and about 1% before the red blood cells are lysed.

7. A process according to claim 1, further comprising the step of extracting at least one lipid from the enriched lipid fraction.

8. A process according to claim 7, further comprising the steps of separating the extracted lipids in a solution, and incubating the solution at a temperature between about −5° C. and about +20° C. to form a precipitate and a liquid phase.

9. A process according to claim 8, wherein the temperature is between about −5° C. and about +10° C.

10. A process according to claim 9, further comprising the step of recovering glycolipids from the precipitate.

11. A process according to claim 10, further comprising the step of recovering phospholipids from the liquid phase.

12. A process according to claim 11, wherein the phospholipid is selected from the group consisting of phophatidylcholine, sphingomyelin, and phosphatidylethanolamine.

13. A process according to claim 9, further comprising the step of recovering hemoglobin from the water soluble fraction.

14. A process according to claim 1, wherein the water soluble pH lowering agent is selected from the group consisting of formic acid, acetic acid, propionic acid, butyric acid, oxalic acid, lactic acid, citric acid, α-ketoglutaric acid, phosphoric acid, hydrochloric acid, sulfuric acid, and mixtures thereof.

15. A process according to claim 14, wherein the water soluble pH lowering agent is selected from the group consisting of citric acid, phosphoric acid, hydrochloric acid, and mixtures thereof.

* * * * *